Figure 4:
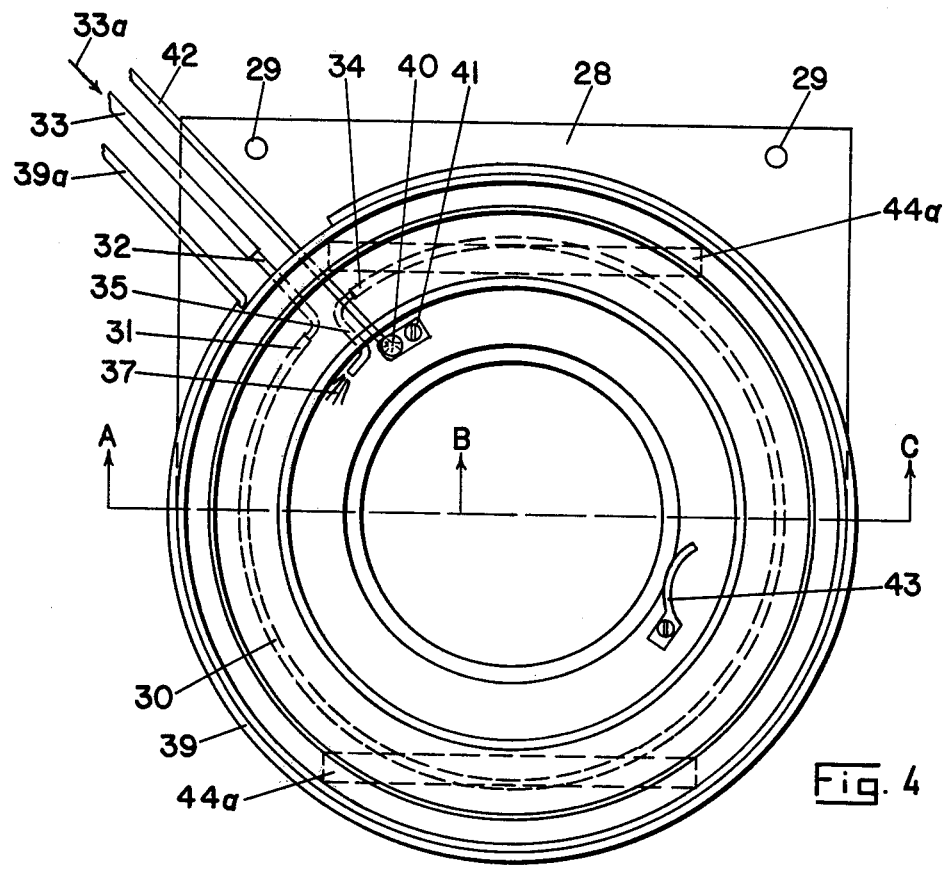

United States Patent [19]

Baker et al.

[11] 4,301,252

[45] Nov. 17, 1981

[54] CONTROLLED ENVIRONMENT INCUBATOR FOR LIGHT MICROSCOPY

[76] Inventors: Fraser L. Baker, 6227 Orange St., Los Angeles, Calif. 90048; John H. Baumann, 836 Wartman Ave., Kingston, Ontario, K7M4M5, Canada

[21] Appl. No.: 137,274

[22] Filed: Apr. 4, 1980

[51] Int. Cl.$^3$ .............................................. C12M 1/38
[52] U.S. Cl. .................................... 435/290; 119/37; 435/298; 435/809
[58] Field of Search ................. 119/37, 15; 435/290, 435/297, 298, 809

[56] References Cited

U.S. PATENT DOCUMENTS

| | | | |
|---|---|---|---|
| 1,893,918 | 1/1933 | Wilson | 119/37 |
| 2,296,930 | 9/1942 | Ihler | 119/37 |
| 2,364,722 | 12/1944 | Kazantzeff | 119/37 |
| 3,562,114 | 2/1971 | Steidel et al. | 435/809 X |
| 3,618,734 | 11/1971 | Khan | 435/809 X |
| 3,854,452 | 12/1974 | Bardet | 119/37 |
| 3,886,047 | 5/1975 | Billups, Jr. | 435/298 |
| 3,926,738 | 12/1975 | Nyiri et al. | 435/290 |
| 4,090,921 | 5/1978 | Sawamura et al. | 435/290 X |
| 4,162,196 | 7/1979 | Folsom et al. | 435/809 X |
| 4,204,037 | 5/1980 | Dill et al. | 435/290 X |

Primary Examiner—Robert J. Warden

[57] ABSTRACT

A miniature, biological incubator for continuous light microscopic observation of cells in cell cultures under environmentally controlled conditions for use in conjunction with petri dishes or similar types of culture dishes, in which different covers are provided to accommodate different types of microscopes and magnification, the incubator being small enough to fit on a microscope stage and to have a sufficiently small internal volume to facilitate maintenance of a controlled atmosphere having stable temperature, humidity and mixture of gases therein and to permit rapid restoration of controlled environment lost during replacement of dishes or during changing of covers to suit particular microscopic observation. The chamber contains a means for humidifying the gases contained therein by evaporation from water-saturated absorbent pads of large surface area, plus a means for humidifying particular gaseous mixtures used to purge the chamber, utilizing at least one hollow fiber tube in intimate contact with water-saturated absorbent pads through which the purging gases are passed, the hollow fiber tube presenting to the purging gases a large wetted surface area resulting in efficient humidification of the purging gases.

8 Claims, 6 Drawing Figures

U.S. Patent  Nov. 17, 1981  Sheet 1 of 2  4,301,252
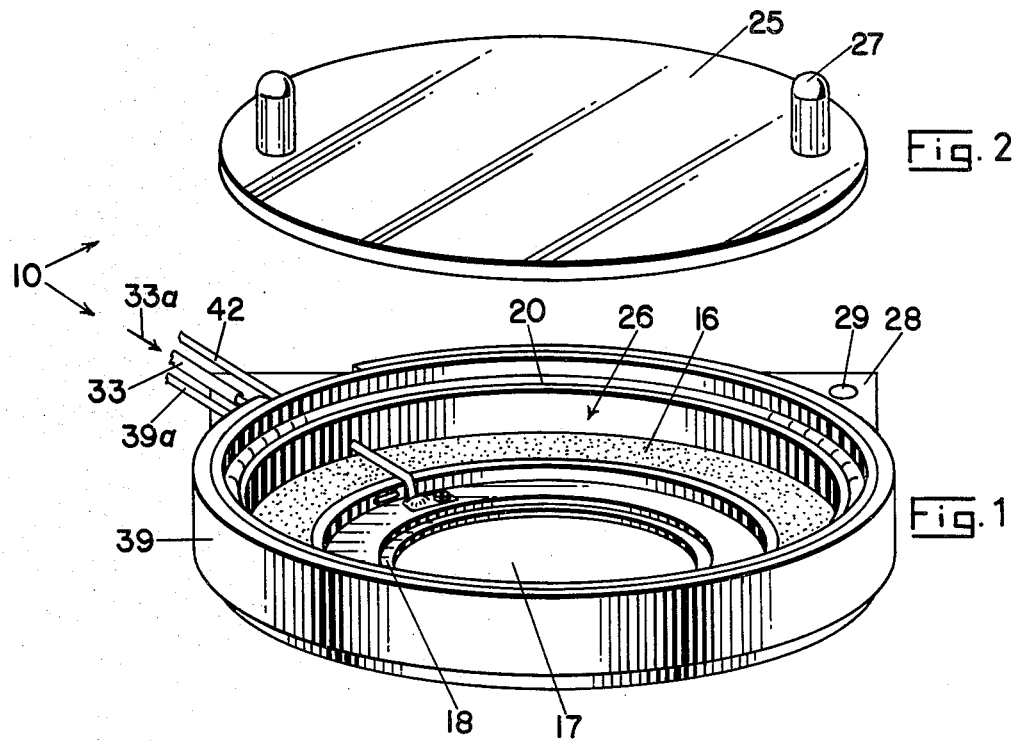
Fig. 2
Fig. 1
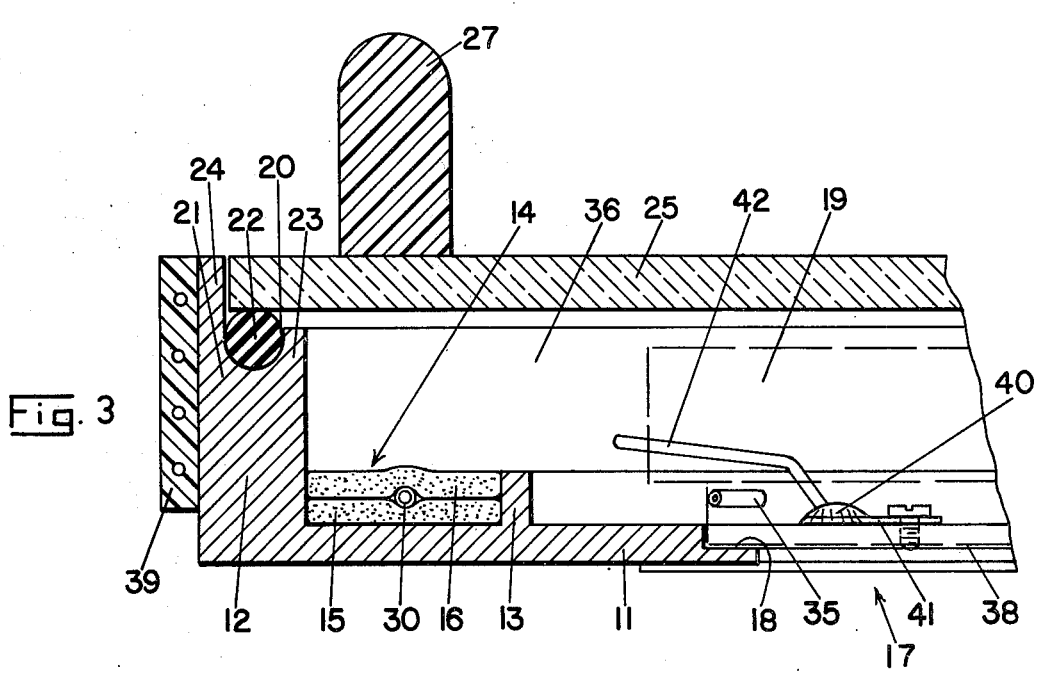
Fig. 3

U.S. Patent    Nov. 17, 1981    Sheet 2 of 2    4,301,252

CONTROLLED ENVIRONMENT INCUBATOR FOR LIGHT MICROSCOPY

This invention relates to biological incubators for light microscopes, and more particularly to biological incubators suitable for continuous microscopic observation of living cell cultures under environmentally controlled conditions.

BACKGROUND AND PRIOR ART

It is frequently desirable to observe biological cells, for a variety of purposes, for extended periods of time. This is generally accomplished by locating cells to be observed, in a suitable medium such as liquid medium or semi-solid medium. Since biological cells require a habitable environment in which to live, microscopic observation of living cell cultures is generally restricted to very short observation periods unless a habitable environment is provided around the cell culture as it rests on a microscope stage, or the microscope is moved into an incubator containing a habitable environment, as is sometimes done in the case of time lapse photography.

Prior art devices have striven to provide a biologically habitable environment around the cell culture as it rests on a microscope stage but have exhibited numerous disadvantages, limiting their usefulness for continuous observation. These prior art devices are usually in the form of plastic boxes that are large and cumbersome, ranging from boxes which enclose the entire microscope to boxes which enclose only the microscope stage. Common for all is that they are difficult to use, requiring large doors on the boxes to allow access, as well as holes to accommodate microscope parts protruding to the outside, such as eyepieces, and mechanical interfaces which enable the microscope to be operated from outside the box. The large size of these prior art devices necessitates a considerable period of time for the restoration of the preselected environment after opening the chamber, for instance to exchange cultures, due to the fact that the preconditioned atmosphere in the chamber is rapidly lost during such an exchange and requires a considerable amount of new prepared atmosphere to restore the environment in the chamber to the proper conditions, the time period required often being too long for the cells to survive.

Another important consideration for observation of cell cultures during extended observation periods, is the need for high humidity to prevent dehydration of the cell culture during such extended observation periods. The prior art devices presently available have the disadvantage that they are unable to maintain high humidity during extended observation periods, since the outside walls of these devices are below the operating temperature required to maintain habitable conditins for the cells in the cell culture, due to the fact that no insulation is provided in such prior art devices. This results in continuous condensation on the entire inside surface of these prior art devices and on the microscope, due to heat loss from parts projecting out from the chamber, such condensation seriously compromising the ability of these devices to maintain high internal humidity and tending in addition to corrode the equipment. Since such condensation also occurs on lenses and the like, cleaning of such surfaces is required before suitable observation may be carried out.

A special gaseous environment, habitable for the culture, is often required and may be maintained by purging the incubator, but since prior art devices are poorly sealed and have a comparatively large internal volume, a high rate of purge is necessary to maintain a desired gaseous environment. Purge gases need to be highly humidified, necessitating the use of accessory humidifying equipment external to the incubator since none of the prior art incubators of this type offer internal humidifying means. Sufficiently thorough sterilization of the prior art devices has also been shown to be extremely difficult.

The present invention overcomes all the aforementioned problems by providing an incubator having a miniature environment chamber that is able to continuously maintain a gaseous environment of high humidity and controlled temperature around a tissue culture dish situated, for example, on a microscope stage.

It is an object of the present invention to provide a miniature incubator that allows continuous observation of cell cultures in a tissue culture dish contained in the incubator, at low or medium objective lens power, using either an upright or inverted microscope, and observation at high objective lens power using an inverted microscope.

It is another object of this invention to provide a miniature incubator that permits continuous observation of a cell culture with video equipment for the purpose of computerized image analysis and cell tracking.

It is still another object of this invention to provide a miniature incubator that allows continuous microscopic observation of living cell cultures, located in disposable tissue culture dishes, by providing a miniature biologically habitable environment around the tissue culture dish, the environment being controlled to maintain a suitable constant temperature, high humidity and ability to be purged with gases suitable for survival of the type of cells being cultured, while the incubator is situated on a microscope stage and attached to the motion controls of the stage.

It is another object of this invention to provide a miniature incubator containing means for effectively humidifying purging gases entering the incubator, in order to maintain a high humidity therein.

It is still another object of this invention to provide a miniature incubator supplied with a plurality of covers to suit various methods of microscopic observation.

Figure 5:
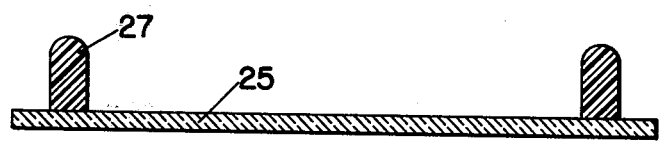
Figure 6:
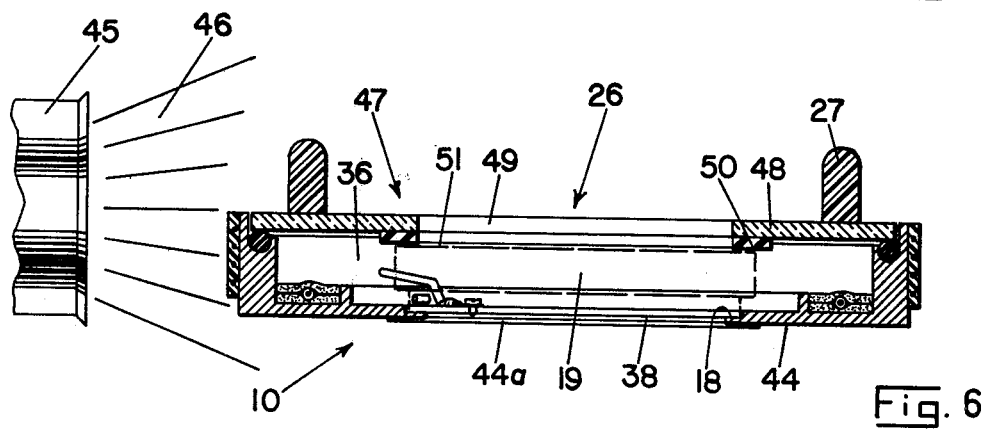

These and other objects and features of the present invention will be apparent from the following detailed description and accompanying drawings in which: FIG. 1 is a perspective view of a miniature incubator, illustrating a preferred form of this invention. FIG. 2 is a perspective view of a transparent cover for the miniature incubator shown in FIG. 1. FIG. 3 is an enlarged fractional, sectional elevation of the miniature incubator shown in FIG. 4 taken on line A-B, a culture dish, shown in phantom, being located therein. FIG. 4 is a plan view of the miniature incubator shown in FIG. 1, illustrating thermal means for maintaining controlled temperature environment within the incubator, and hollow fiber tube, located in the miniature incubator for purging the internal incubator chamber with humidified gases. FIG. 5 is a mid-vertical, cross-sectional view of the transparent cover shown in FIG. 1. FIG. 6 is a mid-vertical, cross-sectional view of the miniature incubator shown in FIG. 4, taken on line A-C, having an alternate cover located thereon, illustrating a preferred method for maintaining a sealed, preselected environmental atmosphere in a closed chamber surrounding the culture dish while permitting a substantially high-power microscope lens to pass through the cover to a close proximity of the upper surface of the culture dish, a culture dish being shown in phantom to illustrate this particular feature, and illustrating an alternate method for maintaining controlled temperature environment within the incubator.

DESCRIPTION OF THE INVENTION

Referring to the drawings, FIG's 1 to 5 show a preferred embodiment of the miniature incubator 10 comprising a base platform 11, having a shallow, upwardly extending, substantially cylindrical outer wall 12, located thereon. A ring-shaped upwardly extending low inner wall 13 is located on platform 11, internally of outer wall 12, forming an annular channel 14 in which moisture soaked annular pads 15 and 16 are located. Platform 11 contains, substantially centrally of low inner wall 13, an observation hole 17 that has a countersink 18 to permit a conventional culture dish 19, shown in phantom, to nest therein. An annular groove 20 is located in upper portion 21 of wall 12 to accommodate a sealing ring such as, for instance, an O-ring 22, groove 20 dividing upper portion 21 into upwardly extending inner lip 23 and upwardly extending peripheral outer lip 24. Inner lip 23 is lower than outer lip 24 to permit a transparent, cylindrical cover plate 25, to be nested within outer lip 23 and rest upon O-ring 22 and thereby seal off upper opening 26 of miniature incubator 10. Handles 27 are located on cover 25 to facilitate removal of cover 25 from incubator 10 as required.

Base platform 11 extends outward from at least one side of wall 12 to provide outward extending portion 28 containing holes 29 to provide means for fastening incubator 10 onto suitable observation means such as, a microscope stage's motion controls (not shown in the drawings). A hollow fiber purging tube 30 is located in annular channel 14, sandwiched between two porous, water-saturated pads 15 and 16, one inlet end 31 of hollow fiber tube 30 being connected to supply tube 32 that passes through wall 12 and is connected externally to supply hose 33 through which suitable gases 33a are fed into hollow fiber purging tube 30. Hollow fiber purging tube 30 extends for a suitable length within annular channel 14, which length can extend for as little as a portion of a turn to more than one full turn to accommodate the particular requirements for humidification. Outlet end 34 of hollow fiber purging tube 30 is connected to purge tube 35 which passes through wall 13 to incubator chamber 36 to supply humidified purge gases 37 into chamber 36 from which purge gases 37 diffuse into aerobic culture dish 19, surplus purge gases escaping through observation hole 17 in base platform 11 by seeping between lower surface 38 of culture dish 19 and countersink 18 that does not form a hermetic seal with lower surface 38 of culture dish 19.

A thermal heating means 39 attached to thermal heating connection 39a which may be, for example, electric, or a warm water jacket joined to a circulating warm water supply, through thermal heater connection 39a, is shown located around wall 12 and in intimate contact therewith, a temperature sensing means 40 such as a thermistor, thermocouple or the like, is located within chamber 36 and held in intimate thermal contact with incubator 10 by clip 41 fastened onto base platform 11, wires 42 extending through wall 12 to suitable external control means for controlling thermal heater 39 to provide suitable survival temperature in incubator 10 to suit the particular cell culture being studied in culture dish 19.

Water saturated pads 15 and 16 accumulate heat from incubator 10 and act as a heat sink permitting some of the water to evaporate and thereby aid in humidifying atmosphere in chamber 36, pads 15 and 16 also serve to heat the purge gasses 37 up to ambient temperature before entering incubator chamber 36. A spring clip 43 is attached to platform 11 and is biased toward culture dish 19 to hold culture dish 19 firmly in place in countrsink 18 to maintain optical alignment of culture cells as incubator 10 is moved back and forth under a microscope lens by microscope stage motion controls. In order to avoid scuffing of under surface 44 of base platform 11, slide strips 44a, for example, in the form of thin adhesive teflon tape, may be located on under surface 44. This also permits incubator 10 to slide freely and easily on a microscope stage as the microscope stage motion controls move incubator 10 back and forth on the microscope stage.

An alternate thermal heating means is shown in FIG. 6 in which a nozzle 45 directs warm air 46 toward and around incubator 10 to provide suitable survival temperature for cell cultures in culture dish 19, temperature of warm air 46 being controlled by temperature sensor 40 that controls amount of heat admitted to nozzle 45.

An alternate cover 47 is shown in FIG. 6, comprising a cover plate 48 having an a viewing aperature 49 centered above culture dish 19, permitting a microscope objective lens to penetrate cover 47 to a location close above culture dish 19 to allow the use of a comparatively high power objective lens and still retain the ability to focus on the cell culture in culture dish 19, when used in conjunction with an upright microscope, or cnversely to permit focusing a light source with a high numerical aperture lens, by placing it closely above culture dish 19 when used in conjunction with an inverted microscope. A peripheral viewing aperature seal 50 is located beneath cover plate 48 surrounding viewing aperature 49 and contacting upper surface 51 of culture dish 19 to provide a substantially closed chamber 36 in incubator 10, permitting purge gases 37 to seep out of chamber 36 only between lower surface 38 of culture dish 19 and countersink 18 of base platform 11.

What is claimed is:

1. A miniature incubator for light microscopes for use in conjunction with a culture dish, comprising a base platform, an outer peripheral wall extending upward from said base platform, said outer peripheral wall having an upper portion, said platform and said outer pheripheral wall providing an incubating chamber having an open end at said upper portion of said wall, cover means for closing said open end, means for nesting and retaining said cover means in said upper portion of said outer peripheral wall, comprising a peripheral recess formed in said upper portion, cover seal means located in said recess between said upper portion and said cover, thermal means for heating said miniature incubator, temperature sensor means for controlling the temperature of said incubator, said temperature sensor means being located within said incubating chamber on said base platform and in intimate contact with said base platform, means for locating said culture dish within said incubator on said base platform, means in said base platform for providing viewing access through the bottom surface of said culture dish, means in said cover for providing viewing access to the top surface of said culture dish, hollow fiber tube purging means in said incubator for conducting purging gases from outside said incubator into said incubator chamber, humidifying means in said incubator chamber for humidifying said gases and said incubator chamber, said hollow fiber purging tube means being in intimate contact with said humidifying means, walls of said hollow fiber purging tube means being suitably porous to permit transmission of humidity from said humidifying means to inside walls of said hollow fiber purging tube means thereby to humidify said gases passing therethrough, and means for attaching said miniature incubator to the stage motion controls of a microscope stage.

2. A miniature biological incubator for light microscopes as claimed in claim 1, in which said means for humidifying said walls of said fiber tube comprises at least one water-soaked pad located in said incubator chamber and surrounding said hollow fiber tube, said at least one pad being located in intimate contact with said hollow fiber tube.

3. A miniature biological incubator for light microscopes as claimed in claim 1, in which said thermal means comprises an electrical heater band located around said upward extending wall, said heater band being in intimate contact with said upward extending wall to permit conduction of heat from said heater band to said incubator and to contents therein, temperature of said heater being controlled by said temperature sensor means.

4. A miniature biological incubator for light microscopes as claimed in claim 1 in which said cover is supplied with handles, suitable for removing and replacing said cover on said upper edge of said wall, said means for providing viewing access to the top surface of said culture dish comprising said cover being manufactured of transparent material.

5. A miniature biological incubator for light microscopes as claimed in claim 1 in which said means for providing viewing access to the top surface of said culture dish comprises a viewing aperture located in said cover, directly above said culture dish, viewing aperature seal means being located between said cover and said top surface of said culture dish, peripherally around said viewing aperture, said cover being supplied with handles for removal of said cover from said upward extending wall, said means for providing viewing access to said under side of said culture dish comprising an aperture located in said platform directly below said culture dish.

6. A miniature biological incubator for light microscopes as claimed in claim 1 in which said means for locating said culture dish in said incubator comprises a recess in said platform suitable for nesting said culture dish therein, and at least one spring clip located on said platform, peripherally of said culture dish and biased against a side of said culture dish to maintain said culture dish firmly in said recess.

7. A miniature biological incubator for light microscopes as claimed in claim 1 in which said means for attaching said incubator to stage motion controls of a microscope stage comprises said base platform having a portion extending outward beyond said peripheral wall, said extending portion being supplied with at least one hole for fastening said incubator to said stage motion controls, and in which low friction slide strips are attached to the underside of said base platform, below said incubator.

8. A miniature biological incubator for light microscopes as claimed in claim 1 in which said thermal means comprises a warm air blower, located externally of said incubator, warm air from said warm air blower being directed toward and around said incubator and temperature of said warm air being controlled by said temperature sensor means.

* * * * *